US012667663B2

(12) United States Patent
Yu et al.

(10) Patent No.: US 12,667,663 B2
(45) Date of Patent: Jun. 30, 2026

(54) AUTOMATED FILLING DEVICE FOR WEARABLE INFUSION PUMP WITH AIR REMOVAL AND DETECTION CAPABILITIES

(71) Applicant: Becton, Dickinson and Company, Franklin Lakes, NJ (US)

(72) Inventors: Bo Yang Yu, Winchester, MA (US); Austin Mckinnon, Herriman, UT (US); J. Richard Gyory, Sudbury, MA (US); Bart Peterson, Farmington, UT (US); Mark Newby, Kamas, UT (US)

(73) Assignee: Becton, Dickinson and Company, Franklin Lakes, CT (US)

( * ) Notice: Subject to any disclaimer, the term of this patent is extended or adjusted under 35 U.S.C. 154(b) by 785 days.

(21) Appl. No.: 17/921,902

(22) PCT Filed: Apr. 26, 2021

(86) PCT No.: PCT/US2021/029059
§ 371 (c)(1),
(2) Date: Oct. 27, 2022

(87) PCT Pub. No.: WO2021/222057
PCT Pub. Date: Nov. 4, 2021

(65) Prior Publication Data
US 2023/0158231 A1     May 25, 2023

Related U.S. Application Data

(60) Provisional application No. 63/017,377, filed on Apr. 29, 2020.

(51) Int. Cl.
*A61M 5/168* (2006.01)
*A61M 5/142* (2006.01)

(52) U.S. Cl.
CPC ...... *A61M 5/1684* (2013.01); *A61M 5/14216* (2013.01); *A61M 5/14248* (2013.01);
(Continued)

(58) Field of Classification Search
CPC ............ A61M 5/1684; A61M 5/14216; A61M 5/14248; A61M 2205/3306;
(Continued)

(56) References Cited

U.S. PATENT DOCUMENTS

| | | | | |
|---|---|---|---|---|
| 4,956,560 A | * | 9/1990 | Smith, Jr. ................. | B67C 3/20 250/577 |
| 2003/0163090 A1 | * | 8/2003 | Blomquist ........ | A61M 5/14244 604/154 |

(Continued)

FOREIGN PATENT DOCUMENTS

| | | |
|---|---|---|
| CN | 86104087 A | 1/1987 |
| CN | 105050638 A | 11/2015 |

(Continued)

OTHER PUBLICATIONS

Japanese Office Action dated Apr. 16, 2024, which issued in a corresponding Japanese Patent Application No. 2022-565966, including Eng. translation.

(Continued)

*Primary Examiner* — Nicolas A Arnett
(74) *Attorney, Agent, or Firm* — Dickinson Wright PLLC

(57) ABSTRACT

A medication filling device and system are provided. The filling device is configured to attach to a medication delivery device and includes a vial attachment component configured to attach to a medication vial. The vial attachment component includes a pump, operable in forward and reverse directions, and an empty vial detection unit configured to detect whether a vial attached to the vial attachment component is empty. The filling device further includes a pro-
(Continued)

cessor configured to receive a signal from the empty vial detection unit indicating whether a vial attached to the vial attachment component is empty, and a user interface configured to output an indication to a user indicating whether the vial is empty.

13 Claims, 9 Drawing Sheets

(52) U.S. Cl.
CPC ............... *A61M 2205/3306* (2013.01); *A61M 2205/3584* (2013.01); *A61M 2205/3592* (2013.01); *A61M 2205/505* (2013.01); *A61M 2209/045* (2013.01)

(58) Field of Classification Search
CPC .. A61M 2205/3584; A61M 2205/3592; A61M 2205/505; A61M 2209/045
See application file for complete search history.

(56) References Cited

U.S. PATENT DOCUMENTS

| | | | |
|---|---|---|---|
| 2005/0148938 A1* | 7/2005 | Blomquist | ........ A61M 5/14244 604/152 |
| 2006/0030822 A1* | 2/2006 | Hung | ................. A61M 39/285 604/246 |
| 2011/0130742 A1* | 6/2011 | Hawkins | ............... A61M 5/158 604/151 |

| | | | |
|---|---|---|---|
| 2012/0078170 A1* | 3/2012 | Smith | ............... A61M 5/14546 604/152 |
| 2012/0078185 A1* | 3/2012 | Smith | ............... A61M 5/14546 604/152 |
| 2015/0151041 A1* | 6/2015 | Yodfat | .................. A61J 1/2089 141/2 |
| 2017/0056590 A1* | 3/2017 | DiPerna | ................. G16H 40/63 |
| 2019/0321556 A1 | 10/2019 | McKinnon | |
| 2023/0055834 A1* | 2/2023 | Cassebee | .............. A61M 5/145 |
| 2024/0017001 A1* | 1/2024 | Lee | ................... A61M 5/14248 |

FOREIGN PATENT DOCUMENTS

| | | |
|---|---|---|
| EP | 1348487 A1 | 10/2003 |
| JP | 2002-529204 A | 9/2002 |
| JP | 2010-510027 A | 4/2010 |
| JP | 2012-148184 A | 8/2012 |
| JP | 2012-196342 A | 10/2012 |
| JP | 2015-529502 A | 10/2015 |
| JP | 2020-504650 A | 2/2020 |
| JP | 2020-32192 A | 3/2020 |
| WO | 8700248 A1 | 1/1987 |
| WO | 2009125398 A2 | 10/2009 |
| WO | 2011/033788 A1 | 3/2011 |
| WO | 2013052414 A2 | 4/2013 |

OTHER PUBLICATIONS

International Search Report dated Aug. 9, 2021, which issued in the corresponding PCT Patent Application No. PCT/US2021/029059.

\* cited by examiner

Liquid Drug

Air

AUTOMATED FILLING DEVICE FOR WEARABLE INFUSION PUMP WITH AIR REMOVAL AND DETECTION CAPABILITIES

CROSS-REFERENCE TO RELATED APPLICATION

This application claims priority from U.S. Provisional Application 63/017,377 filed Apr. 29, 2020, in the United States Patent and Trademark Office, the disclosure of which is incorporated herein by reference in its entirety.

BACKGROUND

1. Field

Apparatuses and methods consistent with example embodiments relate to medication delivery devices and filling devices therefor, and more particularly, to filling devices enabling wireless communication with delivery devices.

2. Description of the Related Art

Diabetes is a group of diseases characterized by high levels of blood glucose resulting from the inability of diabetic patients to maintain proper levels of insulin production when required. Complications from diabetes can be minimized by utilizing one or more treatment options. The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient. Type 1 diabetes (TID) patients are required to take insulin (e.g., via injections or infusion) to move glucose from the bloodstream because their bodies generally cannot produce insulin. Type 2 diabetes (T2D) patients generally can produce insulin but their bodies cannot use the insulin properly to maintain blood glucose levels within medically acceptable ranges.

For the treatment of TID and sometimes T2D, there are two principal methods of daily insulin therapy. In the first method, diabetic patients use syringes or insulin pens to self-inject insulin when needed. Another effective method for insulin therapy and managing diabetes is infusion therapy or infusion pump therapy in which an insulin pump is used. The insulin pump can provide continuous infusion of insulin to a diabetic patient at varying rates to more closely match the functions and behavior of a properly operating pancreas of a non-diabetic person that produces the required insulin. Infusion pump therapy requires an infusion cannula, typically in the form of an infusion needle or a flexible catheter, that pierces the diabetic patient's skin and through which infusion of insulin takes place.

In infusion therapy, insulin doses are typically administered at a basal rate and in a bolus dose. When insulin is administered at a basal rate, insulin is delivered continuously over 24 hours to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates.

Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

An insulin pump may comprise an insulin delivery device that is an integrated device combining most or all of the necessary fluidic components in a single housing. Generally, the housing is adhesively attached to an infusion site on the patient's skin, and does not require the use of a separate infusion or tubing set. A delivery device containing insulin may adhere to the skin and deliver insulin over a period of time via an integrated subcutaneous cannula. Some delivery devices may wirelessly communicate with a separate controller device. Delivery devices are replaced on a frequent basis, such as every three days, or when the medication reservoir is exhausted. Otherwise, complications may occur, such as restriction in the cannula or the infusion site.

When a new delivery device is to be used it is activated and paired with the remote, attached to a patient, and setup is completed via a wireless connection with the remote.

When a new device is first used, it is paired with a wireless controller which programs the device. Current smartphones may be technically capable of all of the wireless controller's operations. However, due to legal restrictions, off-the-shelf smartphones are only permitted to receive data from a delivery device, and cannot be used to send commands or programming to the device.

When a self-injection or self-infusion device is filled from a standard vial, the vial from which it is filled may be emptied before the device is entirely filled.

In delivery device designs, tubes, such as plastic tubes, may be employed as fluid pathways to route fluid flow from one internal component to another. For example, a tube can connect a medication reservoir with a delivery needle. Typically, medication is drawn from the reservoir via a vacuum. However, in such a configuration, it is difficult to remove entrapped air from the medication. This is because the vacuum draws the medication via a negative pressure with respect to atmospheric pressure. Medication at a negative pressure will draw in air instead of releasing air. The presence of air in the delivery device, either in a fill port or a reservoir bag, for example, may cause inaccuracies in delivery of the bolus dose.

SUMMARY

Example embodiments may address at least the above problems and/or disadvantages and other disadvantages not described above. Also, example embodiments are not required to overcome the disadvantages described above, and may not overcome any of the problems described above.

According to an aspect of an example embodiment, a medication filling device is provided, comprising: a vial attachment component comprising: a housing configured to hold a medication vial therein; a pump; an empty vial detection unit configured to detect whether a vial attached to the vial attachment component is empty, a processor configured to receive a signal from the empty vial detection unit indicating whether the vial attached to the vial attachment component is empty; and a user interface configured to output an indication to a user indicating whether the vial is empty.

The empty vial detection unit may comprise a light source, and a light sensor, wherein the light sensor is disposed such that light, output from the light source and transmitted through a vial containing liquid medication, is incident on the light sensor and light, output from the light source and transmitted through a vial empty of medication, is not incident on the light sensor.

The pump may be operable in forward and reverse directions to pump liquid medication between a vial and a medication delivery device.

The user interface may comprise one or more light emitting diodes.

The medication filling device may further comprise a communication circuit operable to transmit a wireless signal.

The communication circuit may comprise an antenna and a match circuit.

The medication filling device may further comprise an upper lid; and a lower case hinged to the upper lid, the lower case configured to receive a medication delivery device therein.

According to an aspect of another example embodiment, a medication filling device is provided, comprising: a housing configured to hold a medication delivery device therewithin; a vial attachment component comprising: a housing configured to hold a medication vial therein; a pump; a processor; a communication circuit operable to transmit a wireless signal to a medication delivery device.

According to an aspect of another example embodiment, a medication filling system comprises a communication circuit operable to receive a wireless signal; a medication filling device comprising: a housing configured to attach to the medication delivery device; a vial attachment component comprising: a housing configured to hold a medication vial therein; a pump; an empty vial detection unit configured to detect whether a vial attached to the vial attachment component is empty, a processor configured to receive a signal from the empty vial detection unit indicating whether the vial attached to the vial attachment component is empty; a user interface output configure to output an indication to a user indicating whether the vial is empty; and a communication circuit operable to transmit a wireless signal.

BRIEF DESCRIPTION OF THE DRAWINGS

The above and/or other example aspects and advantages will become apparent and more readily appreciated from the following description of example embodiments, taken in conjunction with the accompanying drawings in which.

DETAILED DESCRIPTION

Figure 1:
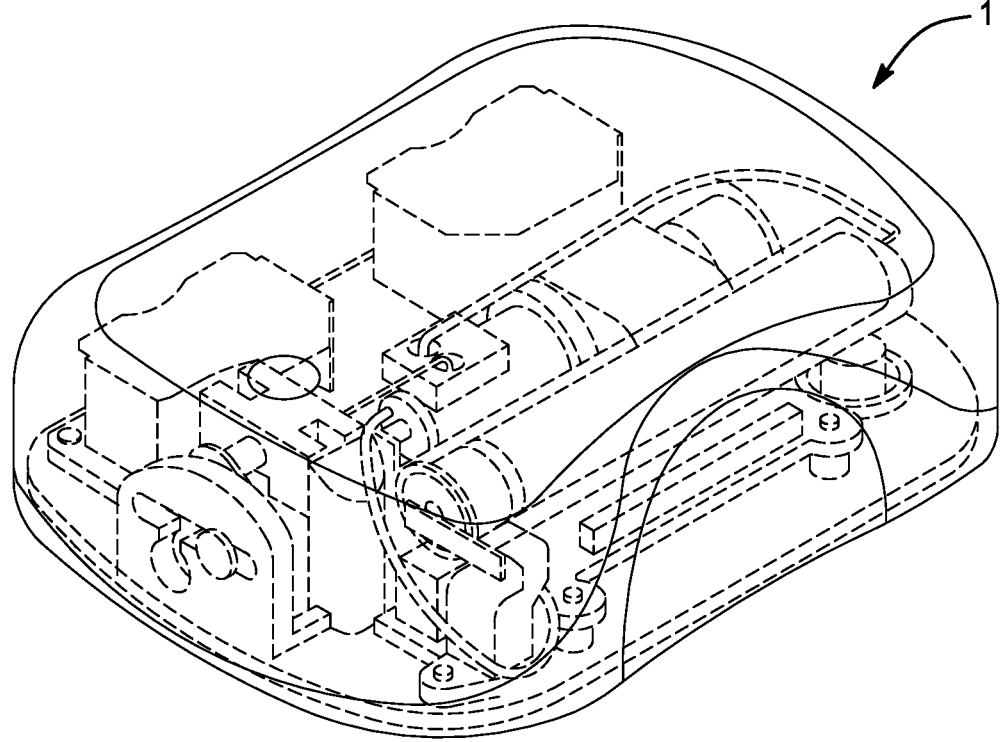
FIG. 1 is a perspective view of a delivery device according to an example embodiment.

Reference will now be made in detail to example embodiments which are illustrated in the accompanying drawings, wherein like reference numerals refer to like elements throughout. In this regard, the example embodiments may have different forms and may not be construed as being limited to the descriptions set forth herein.

It will be understood that the terms "include," "including," "comprise," and/or "comprising," when used in this specification, specify the presence of stated features, integers, steps, operations, elements, and/or components, but do not preclude the presence or addition of one or more other features, integers, steps, operations, elements, components, and/or groups thereof.

It will be further understood that, although the terms "first," "second," "third," etc., may be used herein to describe various elements, components, regions, layers and/or sections, these elements, components, regions, layers and/or sections may not be limited by these terms. These terms are only used to distinguish one element, component, region, layer or section from another element, component, region, layer or section.

As used herein, the term "and/or" includes any and all combinations of one or more of the associated listed items. Expressions such as "at least one of," when preceding a list of elements, modify the entire list of elements and do not modify the individual elements of the list. In addition, the terms such as "unit," "-er (-or)," and "module" described in the specification refer to an element for performing at least one function or operation, and may be implemented in hardware, software, or the combination of hardware and software.

Various terms are used to refer to particular system components. Different companies may refer to a component by different names—this document does not intend to distinguish between components that differ in name but not function.

Matters of these example embodiments that are obvious to those of ordinary skill in the technical field to which these example embodiments pertain may not be described here in detail.

Figure 2:
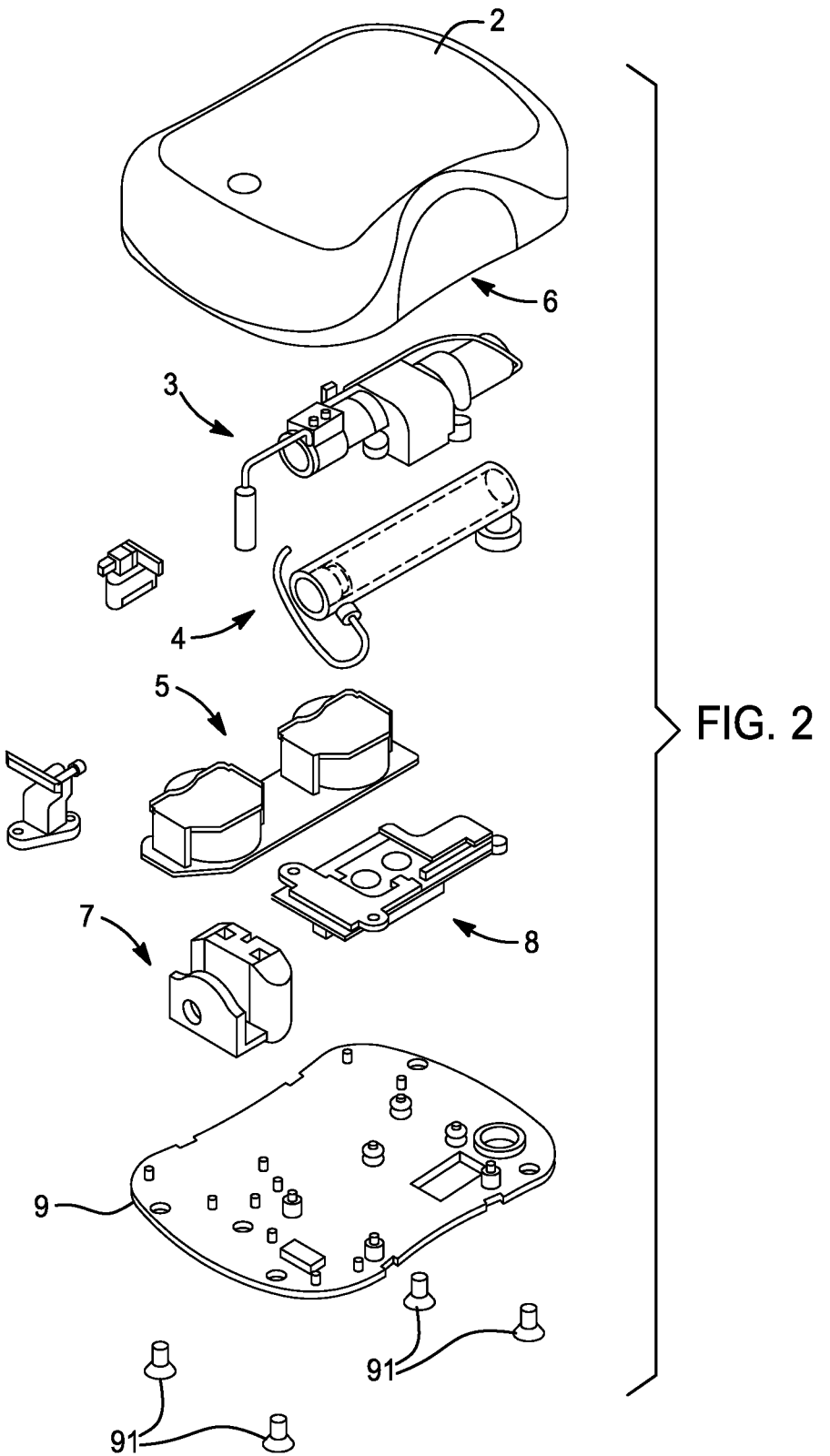
FIG. 2 is an exploded view of the various components of the delivery device of FIG. A, illustrated with a cover.

FIG. 1 is a perspective view of a delivery device 1 according to an example embodiment. The delivery device 1 is illustrated with a transparent cover for clarity and illustrates various components within the delivery device 1. FIG. 2 is an exploded view illustrating various components of the delivery device of FIG. 1. As shown, the device 1 may include: a reservoir 4 for storing insulin or other liquid medication to be injected; a pump 3 for pumping the medication out of the reservoir 4; and a power source 5, which may comprise one or more batteries. An insertion mechanism 7 inserts an inserter needle with a catheter into a patient's skin.

A pair of dose buttons 6 are disposed on a cover 2 for actuating a medication dose, including a basal and/or bolus dosing; and various components may be attached to a base 9 above via one or more fasteners 91. The delivery device 1 also includes various fluid connector lines that transfer medication from the reservoir 4 to an infusion site.

Control electronics control the operations of the device 1 and may comprise communications capabilities for communication with one or more external devices including, but not limited to a remote controller, a personal computer, a smart phone, and a medication filling device, as discussed below.

Figure 3:
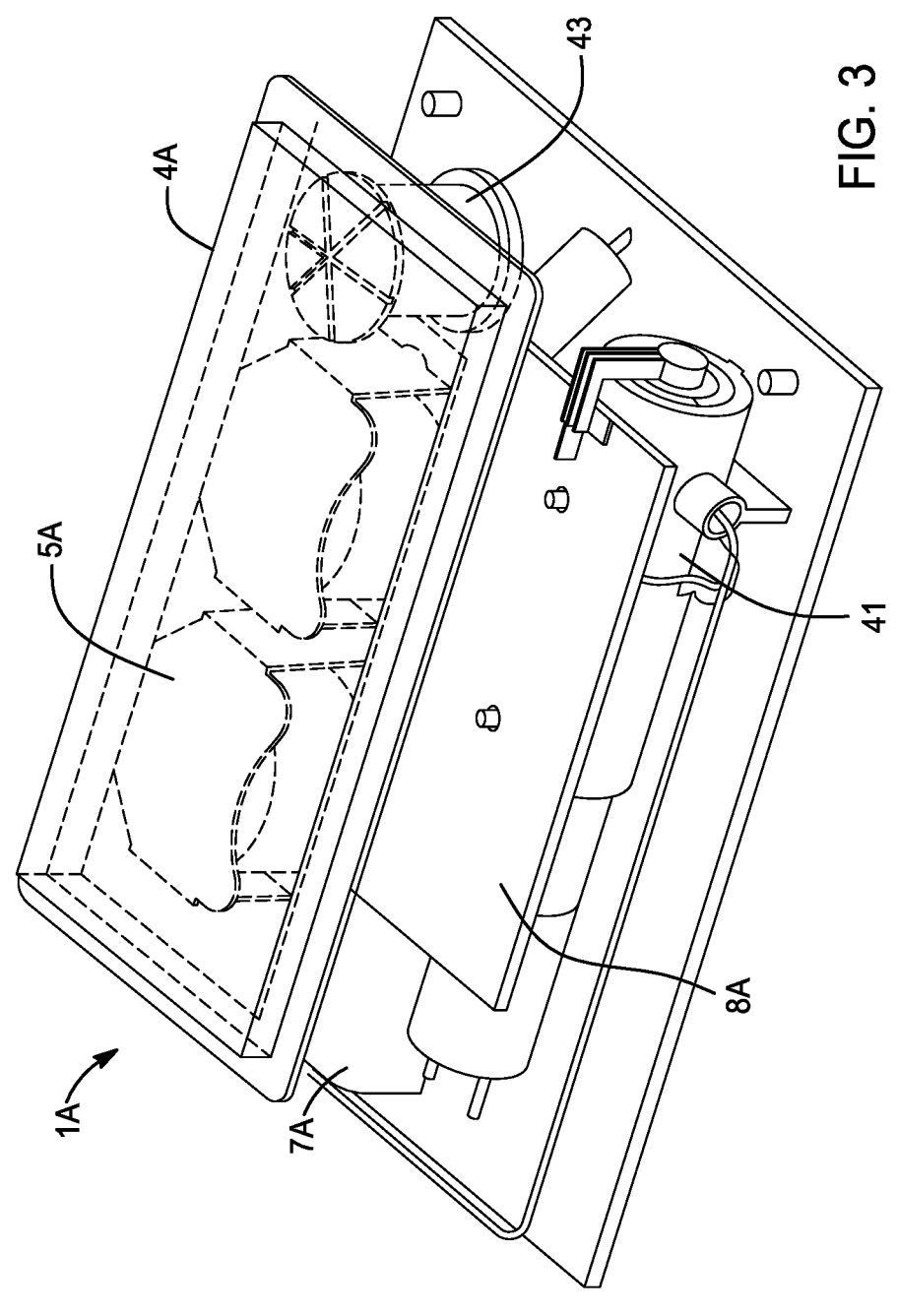
FIG. 3 is a perspective view of an alternative design of a delivery device according to an example embodiment.

FIG. 3 is a perspective view of an alternative design for a delivery device 1A having a flexible reservoir 4A, and illustrated without a cover. Such arrangement may further reduce the external dimensions of the delivery device 1A, with the flexible reservoir 4A filling voids within the device 1A. The patch delivery device 1A is illustrated with a conventional cannula insertion device 7A that inserts the cannula, typically at an acute angle, less than 90 degrees, at the surface of a user's skin. The delivery device 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe to fill the reservoir 4A.

Figure 4:
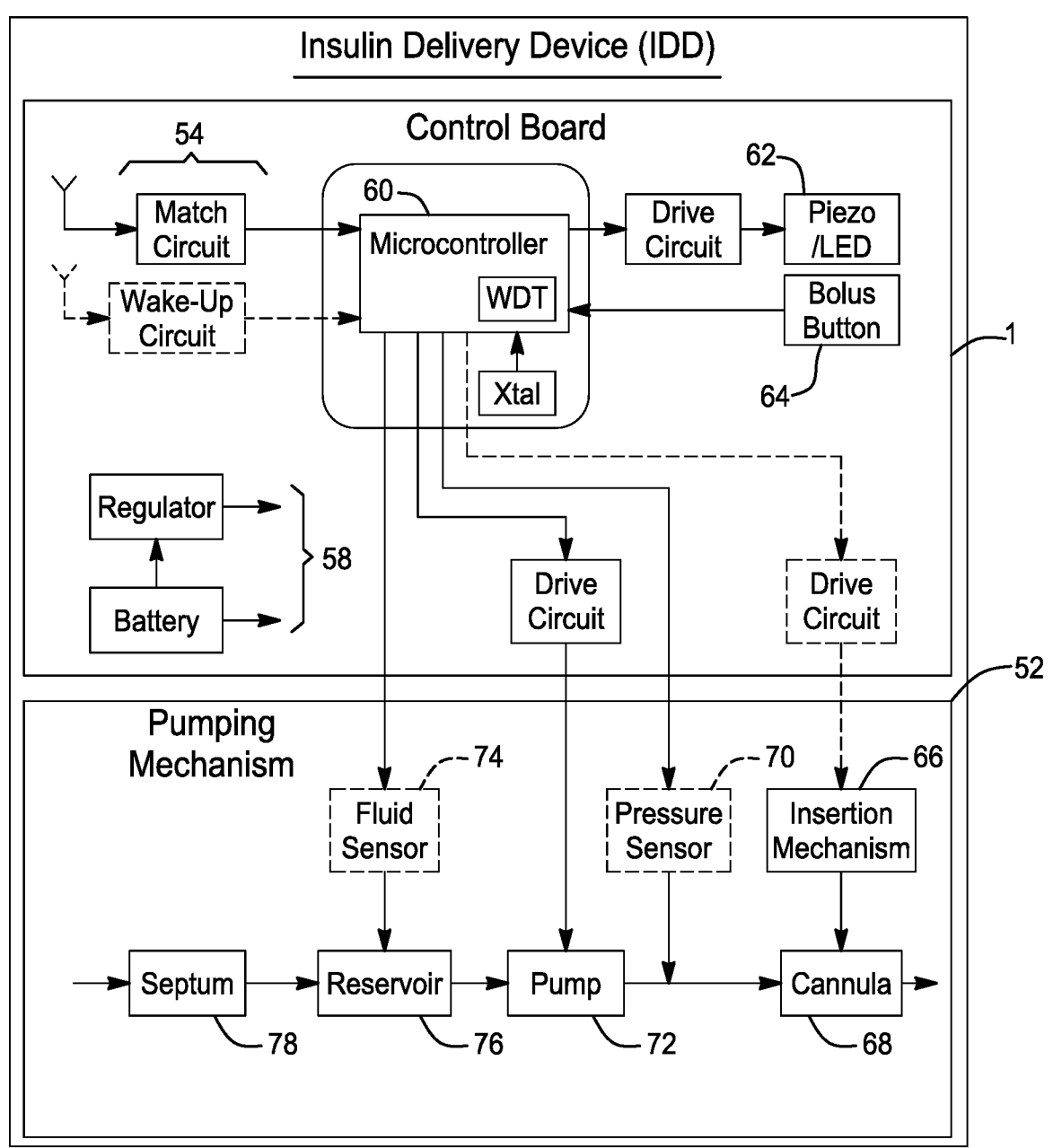
FIG. 4 is a block diagram of a delivery device according to an example embodiment.

FIG. 4 is a block diagram of a delivery device according to an example embodiment. The delivery device may include a microcontroller 60 configured to control a pumping mechanism 52, wireless communication with an external device (e.g., via a communication circuit 54), and pump operations. The RF circuit may comprise a match circuit and one or more antennas, or may comprise another communication circuit, such as a Bluetooth communication circuit. The delivery device includes one or more bolus buttons 64 for manual delivery of medication in addition to any programmed delivery of medication. The pumping mechanism 52 comprises a reservoir 76 for storing a fluid medication (e.g., insulin) to be delivered via a cannula 68 to the patient wearing the device, and a pump 72 for controllably delivering designated amounts of medication from the reservoir through the cannula. The reservoir 76 can be filled via a septum 78 using a syringe. The device may include a manual insertion mechanism 66 for inserting the cannula 68 into a patient. However, the processor 60 can be configured to operate an optional drive circuit to automate operation of the insertion mechanism 66 to deploy the cannula 68 into the patient. The device may also include a fluid sensor 74 and/or a pressure sensor 70. A light emitting diode (LED) 62 can be operated by the microcontroller 60 to turn on and off in one or more steady or flashing patterns to indicate one or more pump operations such as during reservoir priming. The device is powered by a battery and regulator as indicated at 58. When initializing the device 1, the bolus button 64 can be configured as a wake-up button that, when activated by the patient, causes the device to wake from a power conserving shelf mode.

Figures 5, 6A:
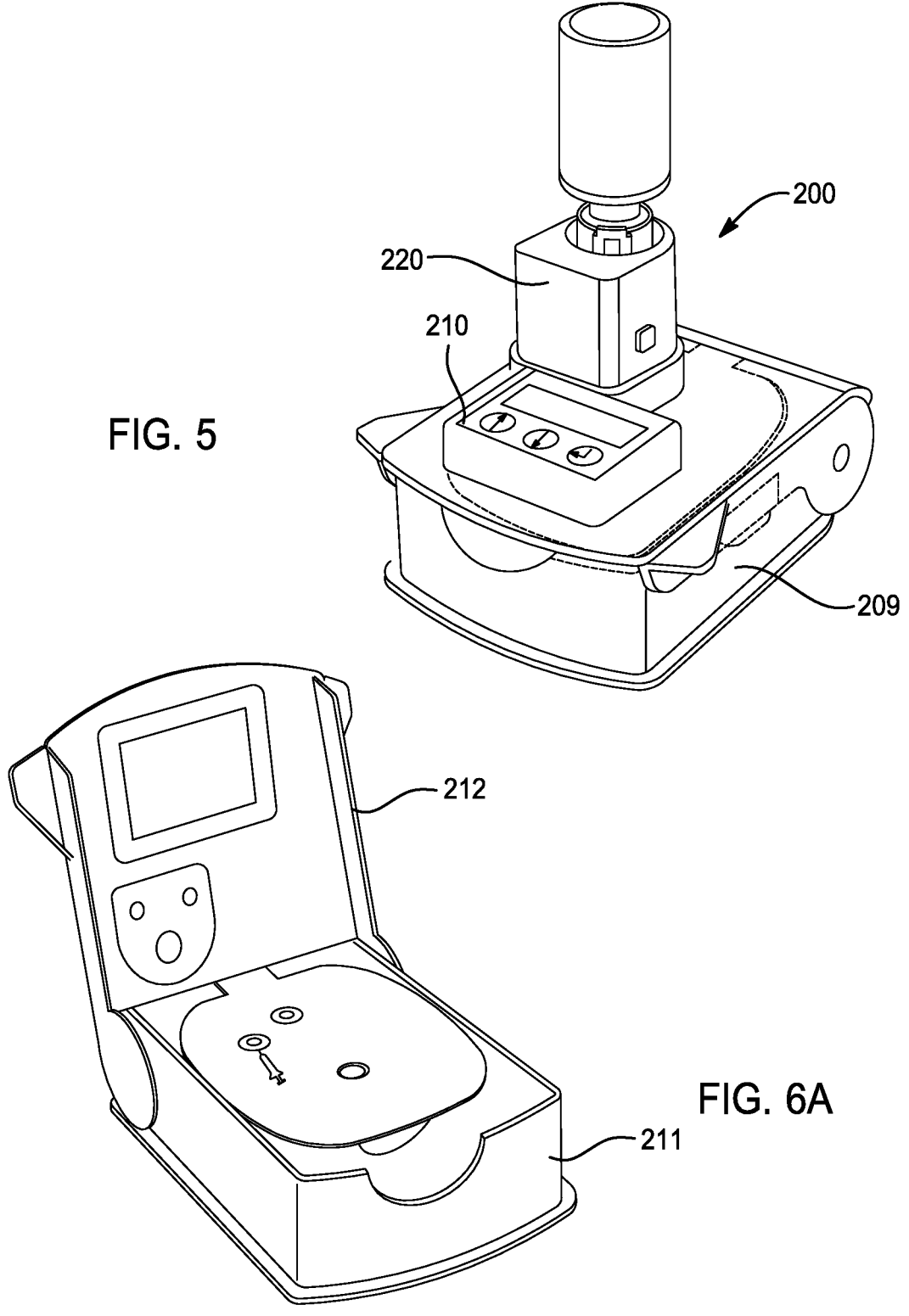
FIG. 5 is a filling device according to an example embodiment.
FIGS. 6A-6C illustrate placement of a delivery device into a base and placement of a vial attachment component onto the base of a filling device, according to an example embodiment.

FIG. 5 illustrates a filling device according to an example embodiment. The filling device 200 includes a base 209 onto which a medication delivery device, such as that of FIG. 1 or FIG. 3, may be attached; and a vial attachment component 220, which may be disposable. The vial attachment component 220 is configured to enable a vial of medication to be attached thereto. The base 209 comprises an electronic component 210, a pump motor (not illustrated), and an empty vial sensor (not illustrated). The vial attachment component 220 comprises a piston pump, a fluid path, one or more needles, and a vial spike (not shown).

Figures 6B, 6C:
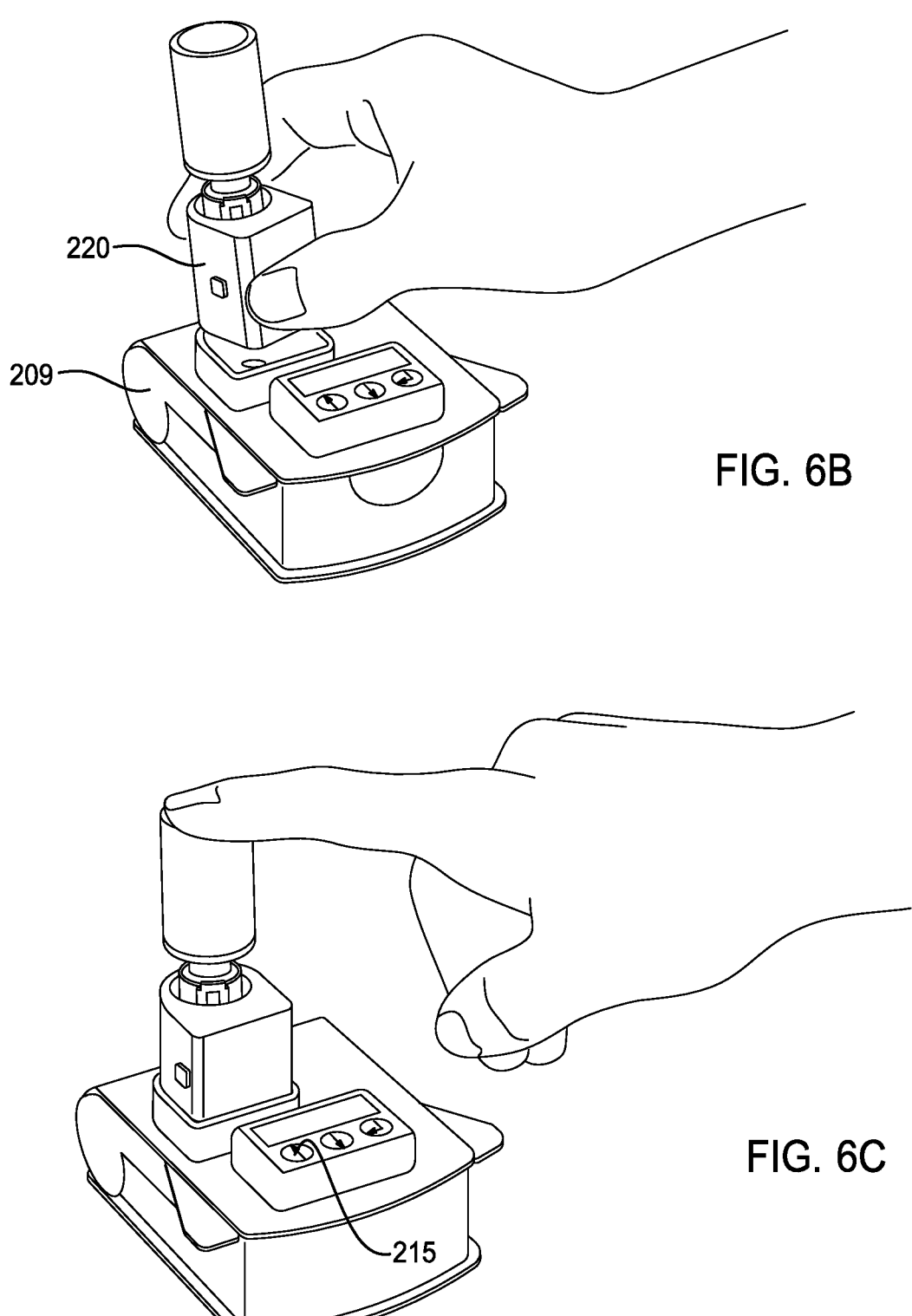

FIGS. 6A-6C illustrate a placement of a medication delivery device 1 into the base 209, according to an example embodiment. As shown, the base 209 may comprise a lower case 211 and an upper lid 212, wherein the lower case 211 may be configured to receive the delivery device therein, and the upper lid 212 may be hinged to the lower case 211 such that once the delivery device is placed within the lower case 211, the upper lid 212 may be closed thereover. Each of the electronic component 210, the pump motor (see, e.g., FIG. 7), and the empty vial sensor (see, e.g., FIGS. 8-9) may be disposed in the upper lid 212, or in the lower case 211. Alternately, instead of the upper lid 212 and lower case 211, the base 209 may comprise a single unit, comprising each of the electronic component 210, the pump motor, and the empty vial sensor, to which the delivery device is attachable.

The vial attachment component 220 comprises a vial spike (not shown) configured to pierce a seal on a vial when the vial is attached to the component 220. The fluid path and vial spike provide communication between the vial and the base 209. As shown in FIG. 6B, the vial attachment component 220 with the vial attached thereto can be mounted onto the base 209. The vial attachment portion 220 may be latched to the base by means of a user pressing down on the vial, as shown in FIG. 6C.

Once the medication delivery device is attached to the base 209 and the vial and vial attachment component 220 is attached to the base 209, a user may initiate filling of the device by pressing or otherwise activating a button 215 on the electronic component 210 of the base 209. The electronic component 210 initiates the pumping mechanism to pump medication from the vial into the delivery device. The pumping mechanism may be any pump configured to operate both in forward and reverse modes, as would be understood by one of skill in the art.

Figure 7:
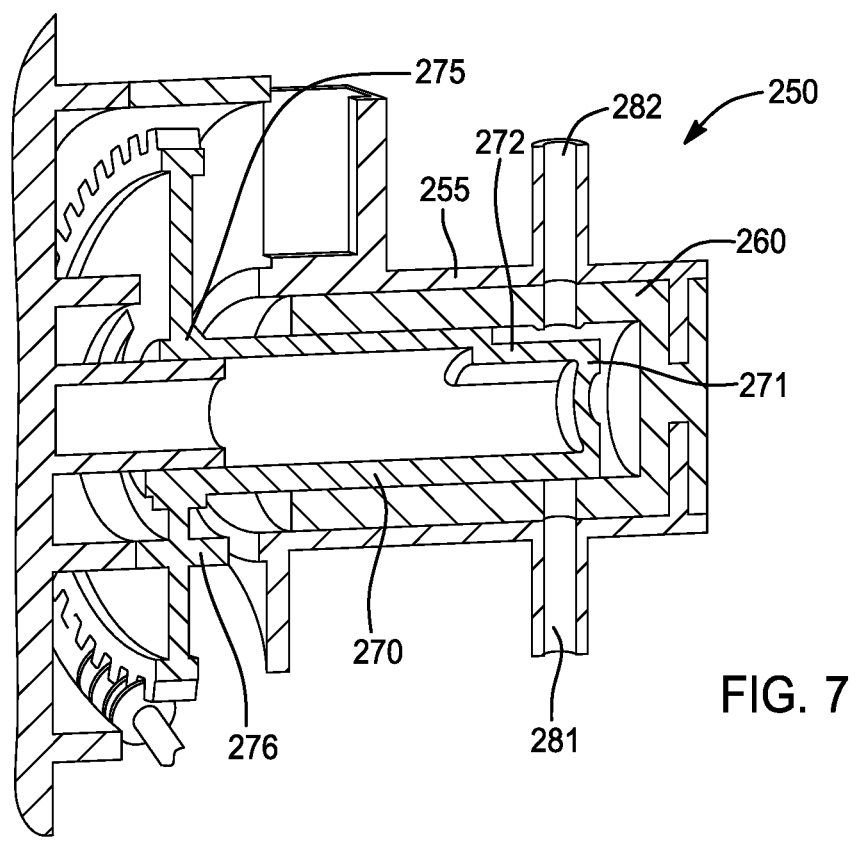
FIG. 7 is a pump mechanism according to an example embodiment.

FIG. 7 illustrates a pump mechanism 250 according to an example embodiment. The pump mechanism is based on a rotary piston pump and comprises a housing 255 having a thermoplastic over-mold seal 260 on an interior surface thereof. The piston 270 has an asymmetric cut 272 at a distal end 271 and a cam surface 276 at a proximal end 275. As the piston is rotated and the cam surface 276 moves the piston 270 in and out of the pump housing 255, the piston rotates and the rotation of the asymmetric cut 272 synchronizes with the opening and closing of the inlet 281 and outlet 282.

As noted above, the pumping mechanism operates in both forward and reverse modes. Accordingly, when activated, for example by a user pressing a button 215 on the electronic component 210 of the base 209, the pump pumps medication from the vial into the delivery device, thus breaking the reservoir bag seal in the delivery device. The pumping mechanism then pumps in reverse to remove any air bubble, prior to returning to the forward mode to fill the delivery device to a desired volume.

Figure 8:
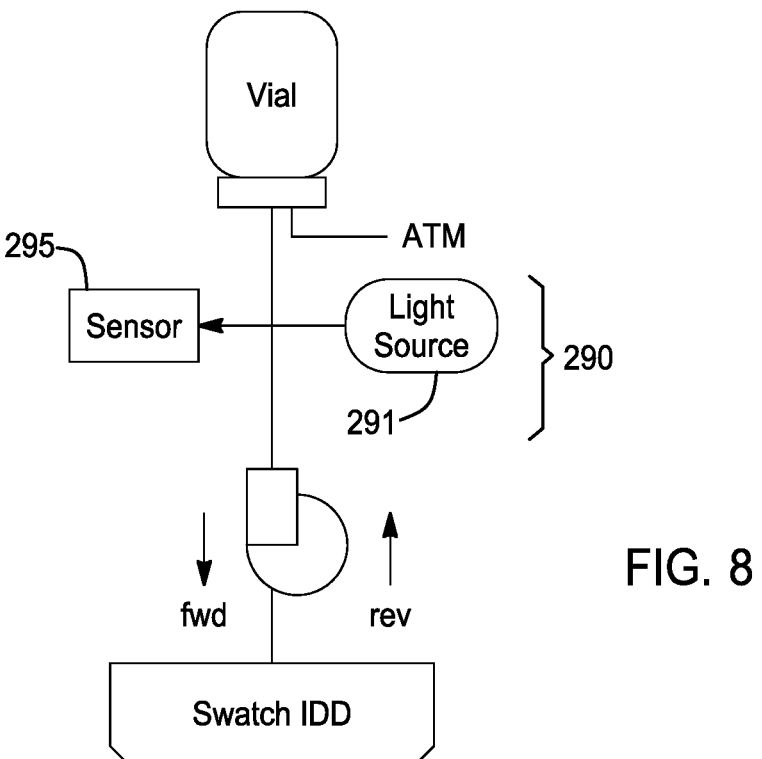
FIG. 8 is a diagram of an empty vial detection sensor according to an example embodiment.
Figure 9A:
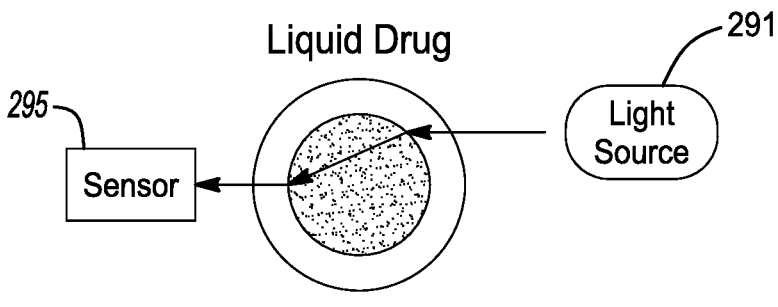
FIGS. 9A and 9B illustrate operation of an empty vial detection sensor according to an example embodiment.
Figure 9B:
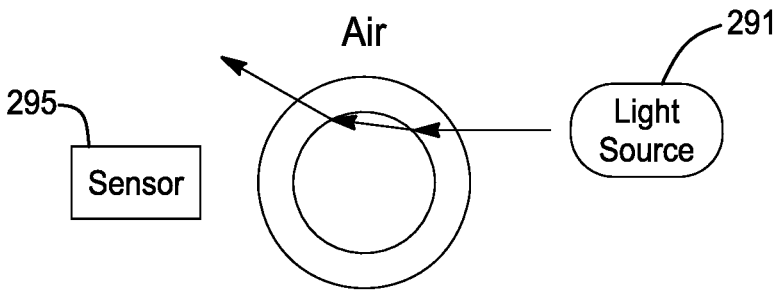

As noted above, the base 209 may include an empty vial detection sensor. FIG. 8 is a diagram of an empty vial detection sensor 290 according to an example embodiment. FIGS. 9A and 9B illustrate an example means of operation of an empty vial detection sensor 290. The sensor 290 includes a light source 291 and a sensor unit 295. As illustrated in FIGS. 9A and 9B, the light source 291 and sensor 295 are positioned with respect to each other such that light emitted from the light source 291, which is transmitted through a vial containing liquid medication, is incident on the sensor 295 and is thereby detectable. When light emitted from the light source is transmitted through an empty vial containing air, the light is not incident on the sensor. Thus, a state of whether the vial contains liquid medication or not may be determined based on whether the sensor detects light from the light source 291 as incident thereon. Alternately, as would be understood by one of skill in the art, the light source 291 and sensor 295 may be disposed in respective positions such that light from the light source 291 is incident on the sensor 295 when transmitted through a vial containing liquid and is not incident on the sensor 295 when transmitted through an empty vial. The electronic component 210 may include one or more output elements, such as a light emitting diode (LED) or other light, a display, or a sound-emitting element. The sensor 295 is communicatively coupled to the electronic component 210, such that, based on a signal received from the sensor, the electronic component can determine a state of whether the vial is empty, and can control the one or more output elements to signal to a user the state of the vial.

Returning to the delivery device itself, the device may be configured for continuous subcutaneous delivery of insulin at set and variable basal (24-hour period) rates and bolus (on-demand) doses for the management of patients with T2D, requiring insulin therapy. It is to be understood, however, that the medical device can be any on-body medical device (e.g., wearable infusion pump, continuous glucose meter) or body area network (BAN) medical device (e.g., handheld blood glucose meter, smart phone with medical condition management apps, or wireless controller for on-body device).

The device may be configured for a patient to wear for a period of three days (up to 84 hours), for example, and thus may have four main functions: delivering a user-set daily basal insulin rate; delivering a user-set bolus insulin amount; delivering manual bolus insulin dose(s); and generating system status and notifications. It is to be understood, however, that the medical device can be used to deliver any type of fluid and is not limited to insulin delivery or to T2D treatment regimens.

Upon initial application to a patient, the device must be programmed, for example with a daily basal insulin rate and a meal-time insulin amount for the particular patient. The device must also be controllable to enable a patient to control the delivery of an additional dose, if needed.

Figure 10:
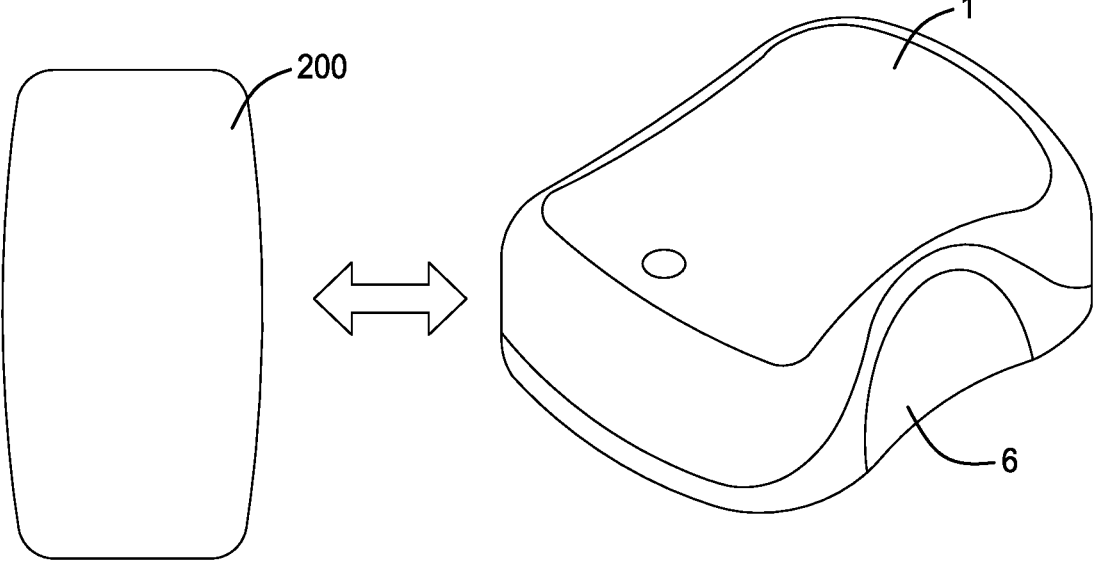
FIG. 10 illustrates a filling device in communication with a delivery device, according to an example embodiment.

FIG. 10 illustrates a filling device 200 configured to communicate with and control a delivery device 1 according to an example embodiment. As discussed above with respect to FIG. D, the delivery device 1 may include one or more bolus buttons 6 for manual delivery of medication, a micro-controller 60, and a communication circuit 54. When initializing the delivery device 1, for example powering-on the device to begin pairing with the filling device 200, the bolus button 6 can be configured as a wake-up button that, when activated by a user, causes the delivery device 1 to wake from a power-conserving shelf mode.

Figure 11:
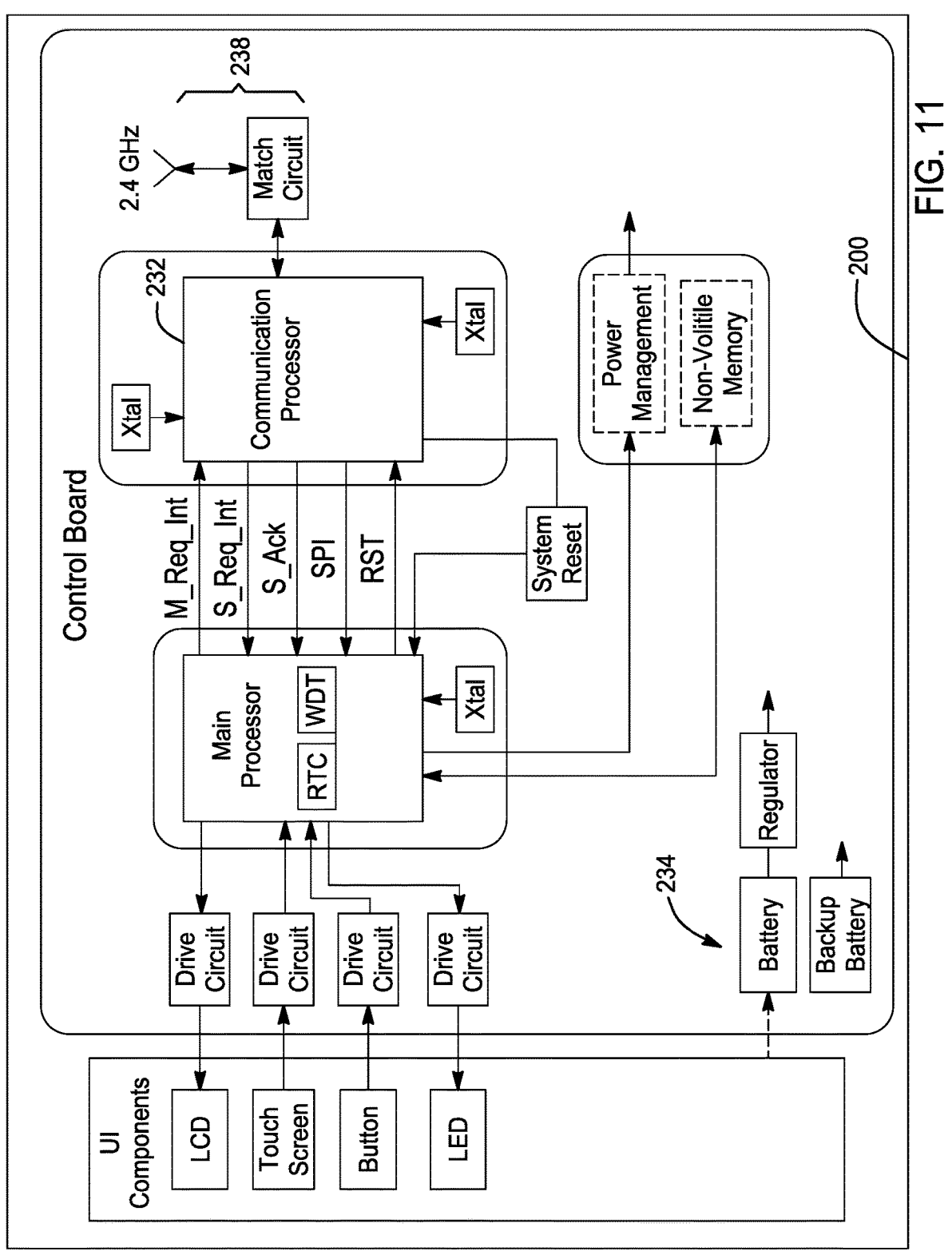
FIG. 11 is a block diagram of a filling device according to an example embodiment.

FIG. 11 is a block diagram of a filling device according to an example embodiment. The filling device 200 includes a main processor and a communications processor 232. The main processor is connected to user interface (UI) components, such as an LCD display with touch screen, one or more buttons, an LED indicator, and the like. The communications processor 232 is connected to radio frequency (RF) components 238 (e.g., an antenna and a match circuit) and is mainly responsible for the filling device's wireless communication with the delivery device 1. The two processors communicate with each other through a serial peripheral interface (SPI). The two processors can also interrupt each other through two interrupt pins, M_REQ_INT and S_REQ_INT. It is to be understood that the filling device can also be configured as a single processor device. A non-volatile memory (e.g., FLASH memory) is also provided in the filling device.

An LCD with a capacitive touch screen may serve as the visual interface for the user by rendering visual and graphical outputs to the user (e.g., system information, instructions, visual notices, user configurations, data outputs, etc.), and by providing a visual interface for the user to enter inputs (e.g., device operation inputs such as delivery device pairing and set up and dosing, and configuration parameters, and so on). The filling device display with capacitive touch screen detects (at least) single-touch gestures over its display area. For example, the touch screen may be configured for recognizing user tactile inputs (tap, swipe, and button press), allowing for navigation within UI screens and applications. The touch screen may aid in executing specific system functionalities (i.e. delivery device setup and pairing with the filling device, insulin dosing, providing user with dosing history, and delivery device deactivation and replacement with another delivery device, and so on) through specific user interactions. The filling device 200 can also include a button such as a device wake-up button that, when activated by the user, causes the filling device to wake from a power conserving sleep mode. The filling device can also have an LED to indicate low battery status (e.g., indicate low battery state when there are a predetermined number of hours or less of usage remaining).

The filling device 200 radio frequency (RF) interface with the delivery device 1 is, for example, based on a Bluetooth Low Energy or BLE-based communication protocol, although other wireless communication protocols can be used. The filing device 200 and the delivery device 1 may communicate wirelessly within a distance of up to 10 feet or approximately 3 meters, utilizing the ISM band from 2400 MHz to 2480 MHZ spectrum. The filling device 200 may be considered as the central device or master, and the delivery device 1 is the peripheral device or slave. Whenever the main processor wants to send information to the delivery device 1 or retrieve information from the delivery device 1, it does so by interacting with the communications processor 232, which in turn, communicates with the delivery device 1 across the BLE link via the respective RF circuits.

The software architecture of the filling device 200 may be configured to control initial setup of the delivery device 1, when initially paired thereto.

The components of the illustrative devices, systems and methods employed in accordance with the illustrated embodiments described herein can be implemented, at least in part, in digital electronic circuitry, analog electronic circuitry, or in computer hardware, firmware, software, or a combination thereof. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or other device or on multiple device at one site or distributed across multiple sites and interconnected by a communication network. Also, functional programs, codes, and code segments for accomplishing features described herein can be easily developed by programmers skilled in the art. Method steps associated with the example embodiments can be performed by one or more programmable processors executing a computer program, code or instructions to perform functions (e.g., by operating on input data and/or generating an output). Method steps can also be performed by, and apparatuses described herein can be implemented as, special purpose logic circuitry, e.g., a field programmable gate array (FPGA) or an application-specific integrated circuit (ASIC), for example.

The various illustrative logical blocks, modules, and circuits described in connection with the embodiments described herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory (ROM) (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Computer-readable non-transitory media includes all types of computer readable media, including magnetic storage media, optical storage media, flash media and solid state storage media. It should be understood that software can be installed in and sold with a central processing unit (CPU) device. Alternately, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

It may be understood that the example embodiments described herein may be considered in a descriptive sense only and not for purposes of limitation. Descriptions of features or aspects within each example embodiment may be considered as available for other similar features or aspects in other example embodiments.

While exemplary embodiments have been described with reference to the figures, it will be understood by those of ordinary skill in the art that various changes in form and details may be made therein without departing from the spirit and scope as defined by the following claims.

10

What is claimed is:

1. A medication filling device comprising:
a vial attachment component comprising:
a housing configured to hold a medication vial therein,
a pump, and
an empty vial detection unit comprising a light source and a light sensor respectively positioned such that light transmitted from the light source and transmitted through an empty vial is not incident on the light sensor and light transmitted from the light source and transmitted through a vial containing liquid medication is incident on the light sensor;
a processor configured to receive a signal from the empty vial detection unit indicating whether a vial attached to the vial attachment component is empty; and
a user interface configured to output an indication to a user indicating whether the vial is empty.

2. The medication filling device of claim 1, wherein the pump is operable in forward and reverse directions to pump liquid medication between a vial attached to the vial attachment component and a medication delivery device.

3. The medication filling device of claim 1, wherein the user interface comprises one or more light emitting diodes.

4. The medication filling device of claim 1 further comprising a communication circuit operable to transmit a wireless signal.

5. The medication filling device of claim 4, wherein the communication circuit comprises an antenna and a match circuit.

6. The medication filling device of claim 4, wherein the processor is configure to control an initial setup of a medication delivery device via the wireless signal transmitted via the communication circuit.

7. The medication filling device of claim 1, further comprising:
an upper lid; and
a lower case hinged to the upper lid, the lower case configured to receive a medication delivery device therein.

8. A medication filling system comprising:
a medication delivery device comprising a communication circuit operable to receive a wireless signal; and
a medication filling device comprising:
a housing configured to attach to the medication delivery device,
a vial attachment component comprising:
a housing configured to hold a medication vial therein,
a pump,
an empty vial detection unit comprising a light source and a light sensor respectively positioned such that light transmitted from the light source and transmitted through an empty vial is not incident on the light sensor and light transmitted from the light source and transmitted through a vial containing liquid medication is incident on the light sensor, and
a processor configured to receive a signal from the empty vial detection unit indicating whether a vial attached to the vial attachment component is empty;
a user interface output configure to output an indication to a user indicating whether the vial is empty; and
a communication circuit operable to transmit a wireless signal.

9. The medication filling system of claim 8, wherein the pump is operable in forward and reverse directions to pump liquid medication between a vial attached to the vial attachment component and a medication delivery device.

10. The medication filling system of claim 8, wherein the user interface output comprises one or more light emitting diodes.

11. The medication filling system of claim 8, further comprising a communication circuit operable to transmit a wireless signal.

12. The medication filling system of claim 11, wherein the communication circuit comprises an antenna and a match circuit.

13. The medication filling system of claim 8, further comprising:

an upper lid; and a lower case hinged to the upper lid, the lower case configured to receive a medication delivery device therein.

\* \* \* \* \*